(12) United States Patent
Ahn

(10) Patent No.: US 11,857,435 B2
(45) Date of Patent: Jan. 2, 2024

(54) ANGLE-EXPANDABLE SPINAL CAGE

(71) Applicants: GBS Commonwealth Co., Ltd., Seoul (KR); PMT Republic, Inc., Walnut, CA (US); Kyoung Gee Ahn, Seoul (KR)

(72) Inventor: Kyoung Gee Ahn, Seoul (KR)

(73) Assignees: Kyoung Gee Ahn, Seoul (KR); GBS Commonwealth Co., Ltd., Seoul (KR); PMT Republic, Inc, Walnut, CA (US)

( * ) Notice: Subject to any disclaimer, the term of this patent is extended or adjusted under 35 U.S.C. 154(b) by 0 days.

(21) Appl. No.: 17/871,871

(22) Filed: Jul. 22, 2022

(65) Prior Publication Data
US 2023/0095997 A1    Mar. 30, 2023

(30) Foreign Application Priority Data
Sep. 30, 2021 (KR) .......................... 10-2021-0129912

(51) Int. Cl.
*A61F 2/44* (2006.01)
*A61F 2/30* (2006.01)

(52) U.S. Cl.
CPC .... *A61F 2/4455* (2013.01); *A61F 2002/3054* (2013.01); *A61F 2002/30433* (2013.01); *A61F 2002/30471* (2013.01); *A61F 2002/30579* (2013.01)

(58) Field of Classification Search
CPC ...... A61F 2/44–447; A61F 2002/30433; A61F 2002/30471; A61F 2002/3054; A61F 2002/30579
See application file for complete search history.

(56) References Cited

U.S. PATENT DOCUMENTS

| | | | | |
|---|---|---|---|---|
| 6,835,206 | B2 * | 12/2004 | Jackson | A61F 2/4611 |
| | | | | 623/908 |
| 2012/0185049 | A1 * | 7/2012 | Varela | A61F 2/447 |
| | | | | 623/17.16 |
| 2015/0173917 | A1 * | 6/2015 | Radcliffe | A61F 2/4611 |
| | | | | 623/17.16 |
| 2018/0036138 | A1 * | 2/2018 | Robinson | A61F 2/4611 |
| 2018/0104066 | A1 * | 4/2018 | Bae | A61F 2/4455 |
| 2021/0236298 | A1 | 8/2021 | Weiman et al. | |
| 2021/0275318 | A1 | 9/2021 | Reimels | |

FOREIGN PATENT DOCUMENTS

KR    10-2147077 B1    8/2020

* cited by examiner

*Primary Examiner* — Nicholas J Plionis
(74) *Attorney, Agent, or Firm* — NKL LAW; Jae Youn Kim

(57) ABSTRACT

Disclosed is an angle-expandable spinal cage including an upper plate and a lower plate disposed to face each other, a frame disposed between the upper plate and the lower plate, the frame having a space formed therein, a block disposed between the upper plate and the lower plate and disposed in front of the frame, and a driving bolt having one end thereof connected to the frame and a remaining end thereof connected to the block. The angle-expandable spinal cage is implanted into an affected area while occupying the minimum angle thereof and to be expanded between vertebral bodies.

18 Claims, 17 Drawing Sheets

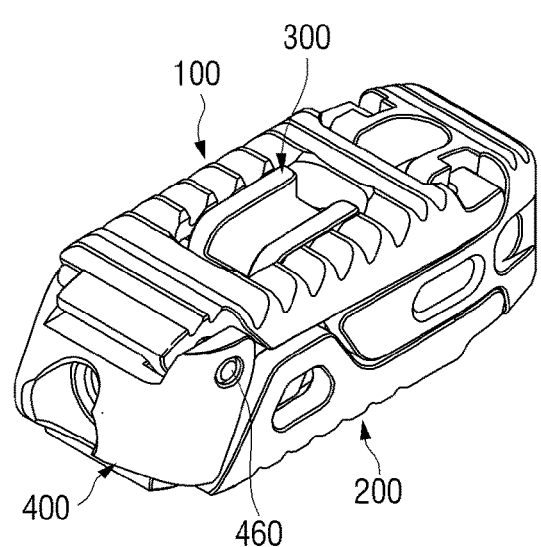 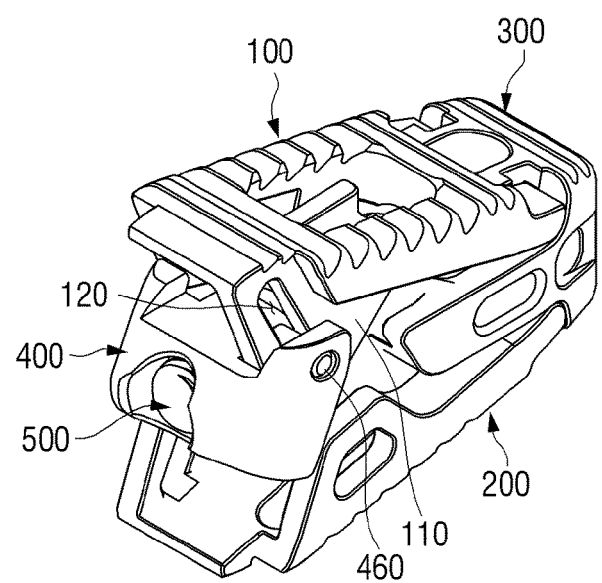
FIG. 1A　　　　　　　　　　FIG. 1B
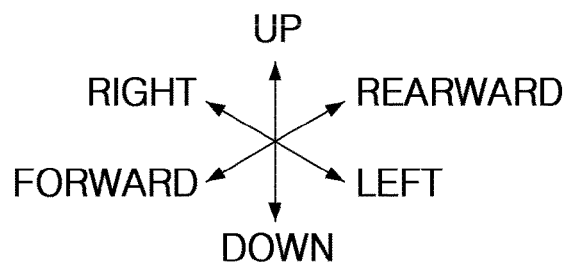

ANGLE-EXPANDABLE SPINAL CAGE

BACKGROUND OF THE INVENTION

Field of the Invention

The present invention relates to a spinal cage, and more particularly to an angle-expandable spinal cage configured to enable adjustment of the angle of each of an upper plate and a lower plate with respect to a frame by operating a driving bolt.

Description of the Related Art

The spine may have problems related to alignment thereof due to congenital abnormalities, degenerative abnormalities, or other reasons such as an accident, or may have structural problems such as a narrow gap between vertebral bodies. Representative spinal diseases include spinal deformity, spinal fracture, disc herniation, spinal stenosis, and facet joint hypertrophy. These spinal diseases require surgical treatment when symptoms thereof worsen and non-invasive treatment becomes ineffective.

Among surgical treatments, spinal fusion is surgery performed as follows. After an intervertebral disc affected by spinal disease is removed, a spinal cage is implanted between vertebral bodies to secure space for bone growth and bone fusion, and the gap between the vertebral bodies is increased to relive pain, thereby restoring the normal curvature of the spine and maintaining the stability of the spine.

In general, the spinal cage used in spinal fusion surgery has a hollow formed therein, and a bone chip is inserted into the hollow. As regeneration occurs around the bone chip, bone fusion occurs between the upper vertebral body and the lower vertebral body.

Various types of spinal cages have been developed for various treatment methods. For example, various efforts have been made to develop a spinal cage having a shape configured so as to be capable of being implanted in the human body to restore the biomechanical stability of the spine.

Since the spinal cage is required to maintain a predetermined distance between the vertebral bodies, the same has a solid structure made of a metal material such as titanium or a titanium alloy having sufficient mechanical strength to support the weight of a human.

However, since a spinal cage of the related art requires an implant path for implantation of the spinal cage into the affected area of a patient suffering from a spinal injury, bone or soft tissue needs to be removed. As a result, surgery may take a long time and side effects may occur due to removal of existing tissue.

The information disclosed in this Background of the Invention section is only for enhancement of understanding of the general background of the invention, and should not be taken as an acknowledgement or any form of suggestion that this information forms the related art already known to a person skilled in the art.

SUMMARY OF THE INVENTION

Therefore, the present invention has been made in view of the above problems, and it is an object of the present invention to provide an angle-expandable spinal cage, configured to be implanted into an affected area while occupying the minimum angle thereof and to be expanded between vertebral bodies.

It is another object of the present invention to provide an angle-expandable spinal cage capable of being usefully used for minimally invasive surgery in a hospital.

The objects of the present invention are not limited to the above-mentioned objects, and other technical objects not mentioned herein will be clearly understood by those skilled in the art from the detailed description of the embodiments.

In accordance with the present invention, the above and other objects can be accomplished by the provision of an angle-expandable spinal cage including an upper plate and a lower plate disposed to face each other, a frame disposed between the upper plate and the lower plate, the frame having a space formed therein, a block disposed between the upper plate and the lower plate and disposed in front of the frame, and a driving bolt having one end thereof connected to the frame and a remaining end thereof connected to the block, wherein an angle of each of the upper plate and the lower plate with respect to the frame is increased or decreased when a distance between the block and the frame is adjusted by operating the driving bolt.

The block may include a block body having a block hole formed in a center thereof, a first inclined part coupled to one side of the block body, the first inclined part having a first inclined surface inclined at a predetermined inclination angle, a second inclined part coupled to the other side of the block body, the second inclined part having a second inclined surface inclined at a predetermined inclination angle, a first inclined accommodation groove formed between the block body and the first inclined part, the first inclined accommodation groove being inclined at a predetermined inclination angle, and a second inclined accommodation groove formed between the block body and the second inclined part, the second inclined accommodation groove being inclined at a predetermined inclination angle.

The upper plate may have a first upper protrusion coupled to one side thereof, the first upper protrusion being accommodated in the first inclined accommodation groove, and a second upper protrusion coupled to the other side thereof, the second upper protrusion being in contact with the second inclined surface of the second inclined part, and the lower plate may have a first lower protrusion coupled to one side thereof, the first lower protrusion being in contact with the first inclined surface of the first inclined part, and a second lower protrusion coupled to the other side thereof, the second lower protrusion being accommodated in the second inclined accommodation groove.

The first inclined surface of the first inclined part and the second inclined accommodation groove may be disposed parallel to each other, and the second inclined surface of the second inclined part and the first inclined accommodation groove may be disposed parallel to each other.

The first inclined part or the second inclined part and the block body may have a restraint pin disposed therebetween and coupled thereto in a transverse direction, and the upper plate or the lower plate may have a long hole formed in a side portion thereof, the long hole being formed to be vertically elongated to correspond to a position of the restraint pin, wherein the restraint pin may be inserted into and accommodated in the long hole so as to be slidable therein.

The frame may include a front part having a front hole formed therein, the front hole allowing one end of the driving bolt to be inserted thereinto, a connection part extending in a longitudinal direction from one end of the front part, and a rear part coupled to one end of the connection part.

The rear part may have at least one upper hinge groove and at least one lower hinge groove formed to be recessed into a side portion thereof, and the upper plate may have an upper hinge part at one end thereof, the upper hinge part being formed to protrude so as to be inserted into and accommodated in the upper hinge groove, and the lower plate may have a lower hinge part at one end thereof, the lower hinge part being formed to protrude so as to be inserted into and accommodated in the lower hinge groove, wherein the upper plate and the lower plate may be rotatable with respect to the upper hinge part and the lower hinge part, respectively.

The upper hinge groove may include an upper curved surface part having a curved inner surface, and an upper coupling passage part connected to an upper portion of the upper curved surface part, and the lower hinge groove may include a lower curved surface part having a curved inner surface, and a lower coupling passage part connected to a lower portion of the lower curved surface part.

The upper hinge part may have an upper hinge curved surface formed at one end thereof, the upper hinge curved surface having a curved surface to correspond to the upper curved surface part of the upper hinge groove, and the lower hinge part may have a lower hinge curved surface formed at one end thereof, the lower hinge curved surface having a curved surface to correspond to the lower curved surface part of the lower hinge groove.

The upper hinge part may have an upper entrance part formed at one end thereof so as to enter the upper coupling passage part, and the lower hinge part may have a lower entrance part formed at one end thereof so as to enter the lower coupling passage part.

The upper entrance part may have a width formed to be equal to or smaller than a width of the upper coupling passage part, and the upper coupling passage part may have the width formed to be smaller than a maximum width of the upper curved surface part, and the lower entrance part may have a width formed to be equal to or smaller than a width of the lower coupling passage part, and the lower coupling passage part may have the width formed to be smaller than a maximum width of the lower curved surface part.

The front part may have a fusion passage formed in an upper surface thereof or a lower surface thereof.

The rear part may have a frame penetration hole formed therein in the longitudinal direction, wherein the frame penetration hole may be connected to an internal space defined by the connection part.

The rear part may have a mechanism-coupling groove formed in a side portion thereof, the mechanism-coupling groove being formed to be recessed.

The driving bolt may have a bolt body having male threads formed on an outer circumferential surface thereof, and a bolt head formed at an end of the bolt body, the bolt head having a diameter larger than a diameter of the bolt body.

The angle-expandable spinal cage may further include a fixing groove formed between the bolt body and the bolt head, the fixing groove having a diameter smaller than the diameter of the bolt body, and a fixing ring inserted into and accommodated in the fixing groove, the fixing ring being formed in a 'C' shape with one side thereof open.

The bolt head may be accommodated in a front hole formed to penetrate through the frame, wherein the front hole may further accommodate a fixing cap to come into contact with an end of the bolt head, the fixing cap being rotatable in the front hole.

The bolt head may have a bolt inclined surface formed at an end thereof, the bolt inclined surface being inclined at a predetermined inclination angle, and the fixing cap, contacting the end of the bolt head, may have a fixing inclined surface formed at an end thereof, the fixing inclined surface being formed to correspond to a shape of the bolt inclined surface, wherein the bolt inclined surface and the fixing inclined surface may be kept in close contact with each other when the fixing cap rotates.

The front hole may have a front end formed therein to allow a fixing end formed to protrude from a side portion of the fixing cap to be in contact with and supported by the front end, the front end being formed to protrude from an inside of the front hole.

The fixing cap may have a plurality of fixing rotation grooves formed in a side portion thereof so that the fixing cap is rotatable, the plurality of fixing rotation grooves being formed to be recessed into the side portion.

BRIEF DESCRIPTION OF THE DRAWINGS

The above and other objects, features, and other advantages of the present invention will be more clearly understood from the following detailed description taken in conjunction with the accompanying drawings, in which:

FIGS. 1A-1B are views showing the overall appearance of an angle-expandable spinal cage according to an embodiment of the present invention;

DETAILED DESCRIPTION OF THE INVENTION

Hereinafter, the present invention will be described in detail with reference to the accompanying drawings so that those skilled in the art to which the present invention pertains can easily implement the present invention. However, the present invention may be implemented in various ways and is not limited to the embodiments described herein.

In order to clearly describe the present invention, parts irrelevant to the description are omitted. Wherever possible, the same reference numbers will be used throughout the drawings to refer to the same or like parts.

In addition, the terms or words used in the specification and claims should not be construed as being limited to conventional or dictionary meanings, but should be interpreted as having meanings and concepts consistent with the technical spirit of the present invention based on the principle that the inventor may appropriately define concepts of the terms in order to describe his or her invention in the best mode.

Figure 2:
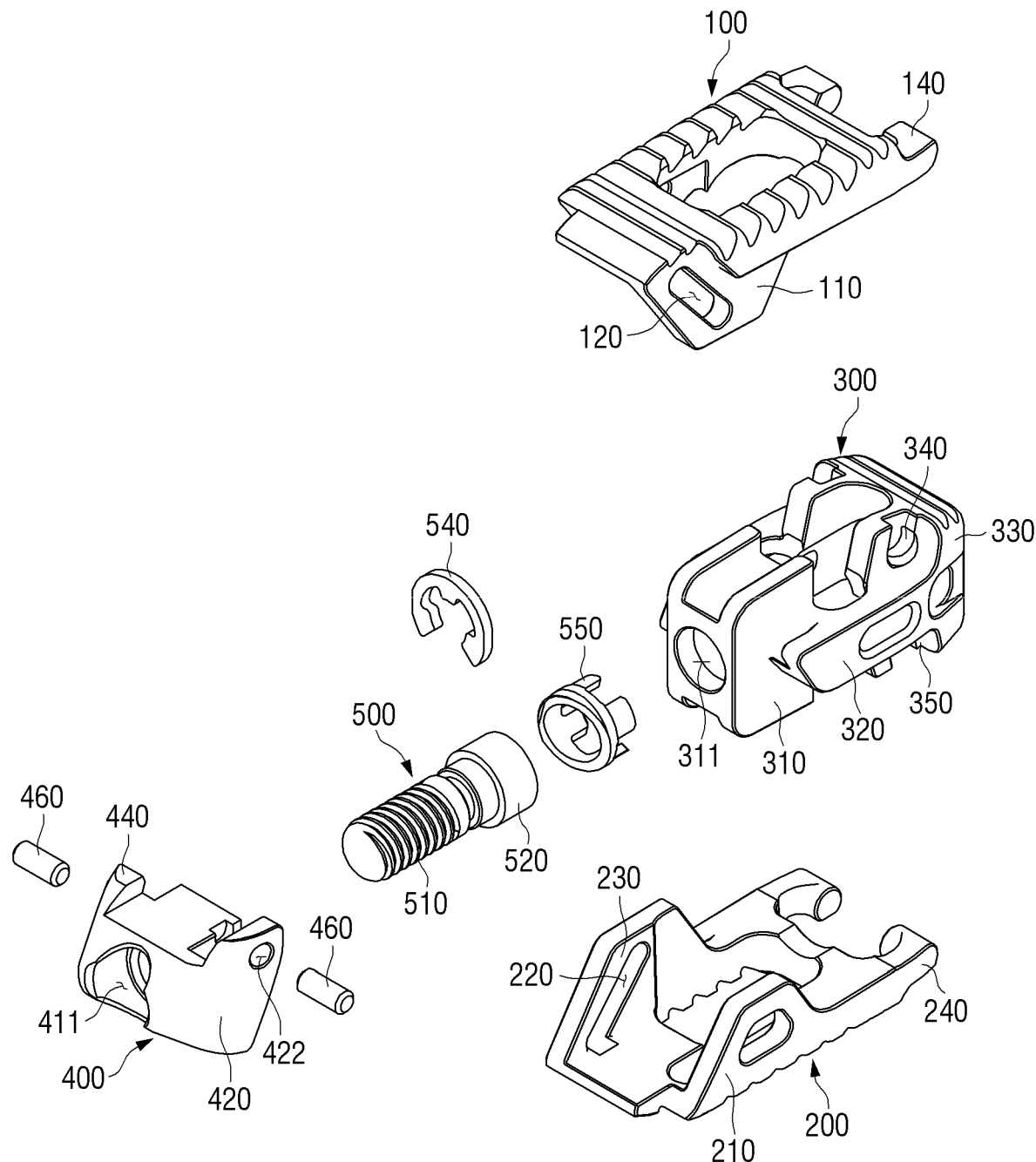
FIG. 2 is a view showing the exploded state of each component of the angle-expandable spinal cage according to the embodiment of the present invention.

FIGS. 1A-1B are views showing the overall appearance of an angle-expandable spinal cage according to an embodiment of the present invention, and FIG. 2 is a view showing the exploded state of each component of the angle-expandable spinal cage according to the embodiment of the present invention.

FIG. 1A is a view showing the state before the angle of the angle-expandable spinal cage according to the embodiment of the present invention is increased, and FIG. 1B is a view showing the state after the angle of the angle-expandable spinal cage according to the embodiment of the present invention is increased.

As shown in FIGS. 1A-1B, the angle-expandable spinal cage according to the present invention includes an upper plate 100, a lower plate 200, a frame 300, a block 400, and a driving bolt 500.

The upper plate 100 is disposed at the upper portion of the frame 300, and the lower plate 200 is disposed at the lower portion of the frame 300. A plurality of teeth are formed on the upper surface of the upper plate 100 and the lower surface of the lower plate 200. Here, the plurality of teeth dig into an upper vertebral body and a lower vertebral body so that the spinal cage has a constant fixing force between the vertebral bodies. The plurality of teeth allow the spinal cage to stably maintain the position thereof at the initial stage of spinal fusion procedures.

Each of the upper plate 100 and the lower plate 200 has a hollow formed therein. The hollow is filled with an autograft, allograft, or synthetic bone to accelerate bone growth.

In the embodiment, the upper plate 100, the lower plate 200, and the frame 300 are together formed in a long bullet shape in the forward-and-rearward direction, but are not limited thereto. The same may be formed in various shapes such as a flat shape, a curved shape, or a disk shape.

The frame 300 is disposed between the upper plate 100 and the lower plate 200. Specifically, the frame 300 includes a front part 310 having a front hole 311 formed therein, a connection part 320 extending in the longitudinal direction from the rear end of the front part 310, and a rear part 330 coupled to the rear end of the connection part 320. A pair of connection parts 320 is provided, and an internal space 321 is defined between the pair of connection parts 320 in the longitudinal direction.

The block 400 is disposed between the upper plate 100 and the lower plate 200, and is disposed in front of the frame 300.

The driving bolt 500 has the rear end thereof connected to the frame 300 and the front end thereof connected to the block 400. The distance between the block 400 and the frame 300 may be increased or decreased by rotating the driving bolt 500. The driving bolt 500 is formed of a bolt body 510, having male threads 511 formed on the outer circumferential surface thereof, and a bolt head 520 formed at the end of the bolt body 510, the bolt head 520 having a diameter larger than that of the bolt body 510.

The front end of the bolt body 510 is rotatably inserted into a block hole 411 in the block 400 to be movable forwards and rearwards, and the bolt head 520 is accommodated in the front hole 311 in the frame 300 to pull the frame 300 forwards and rearwards.

Normally, when the driving bolt 500 moves rearwards, the frame 300 also moves rearwards, and the upper plate 100 and the lower plate 200 maintain a minimum angle therebetween, as shown in FIG. 1A.

After the angle-expandable spinal cage is implanted into an affected area and the driving bolt 500 is moved forwards, the frame 300 also moves forwards, thereby moving the upper plate 100 and the lower plate 200 forwards. Accordingly, as shown in FIG. 1B, the angle of each of the upper plate 100 and the lower plate 200 with respect to the frame 300 is increased, thereby making it possible to increase the angle between the vertebral bodies.

As described above, according to the present invention, the angle-expandable spinal cage may be implanted into the affected area while occupying the minimum angle thereof and may then be expanded between the vertebral bodies, thereby having an effect of being usefully used for minimally invasive surgery.

Figure 3:
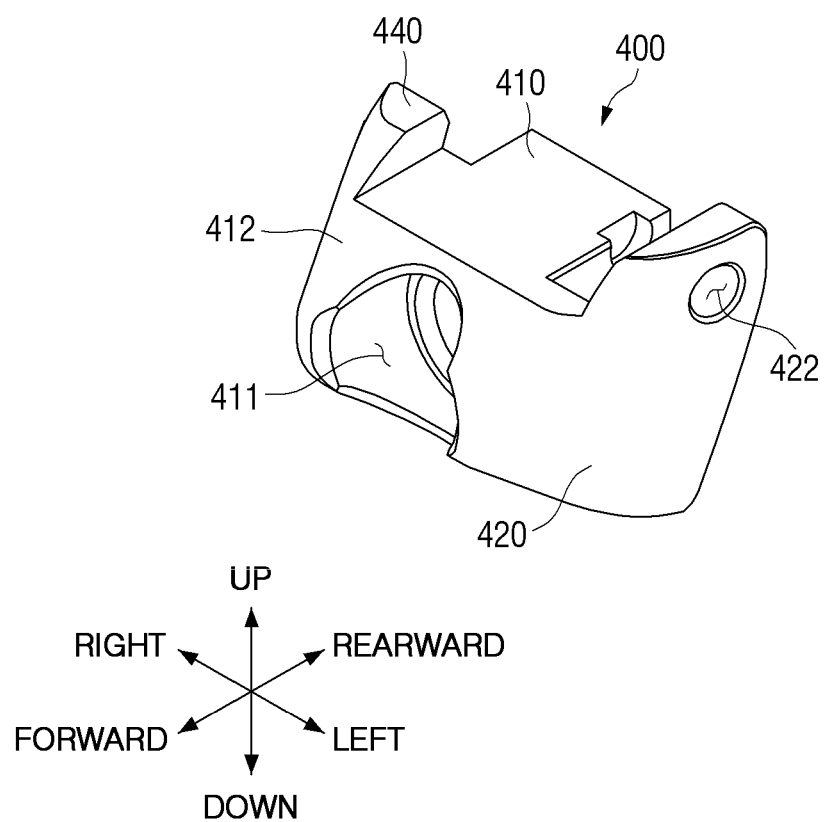
FIG. 3 is a view showing a block according to the embodiment of the present invention, seen from the front.
Figure 4:
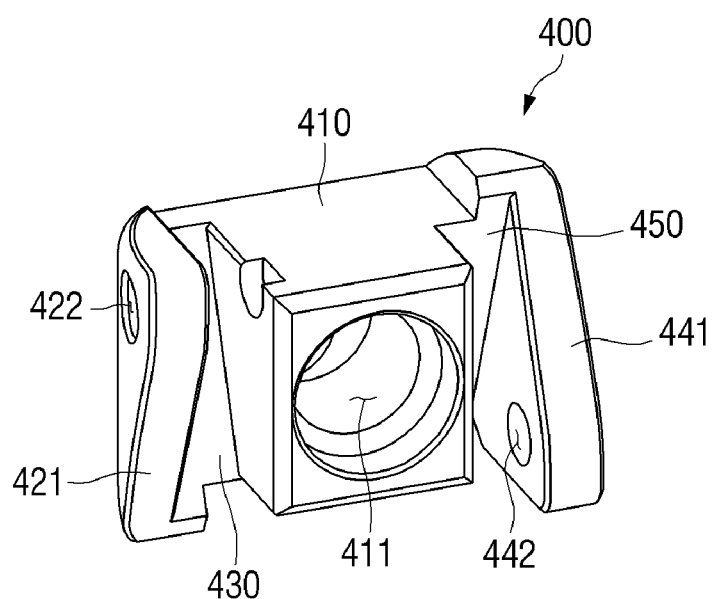
FIG. 4 is a view showing the block according to the embodiment of the present invention, seen from the rear.
Figure 4:
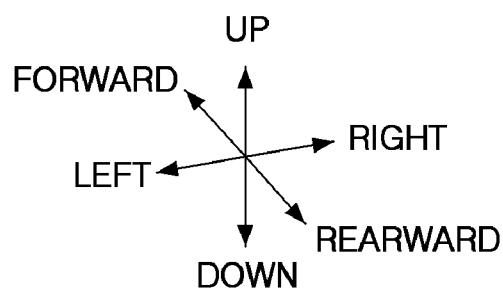
Figure 5A:
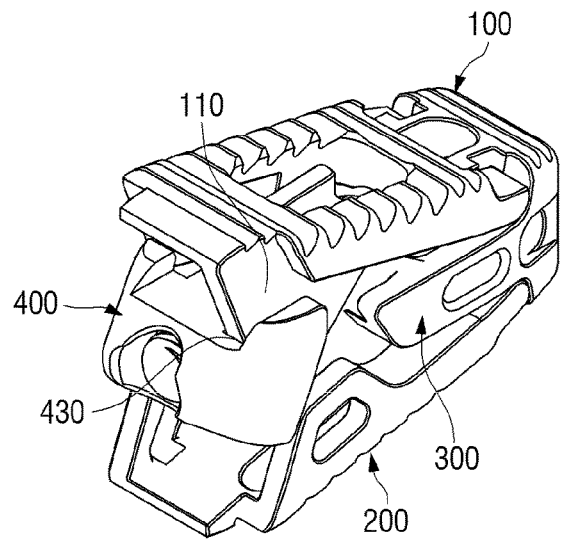
FIGS. 5A-5B are views showing a portion at which an upper plate and the block according to the embodiment of the present invention are in contact with each other.
Figure 5B:
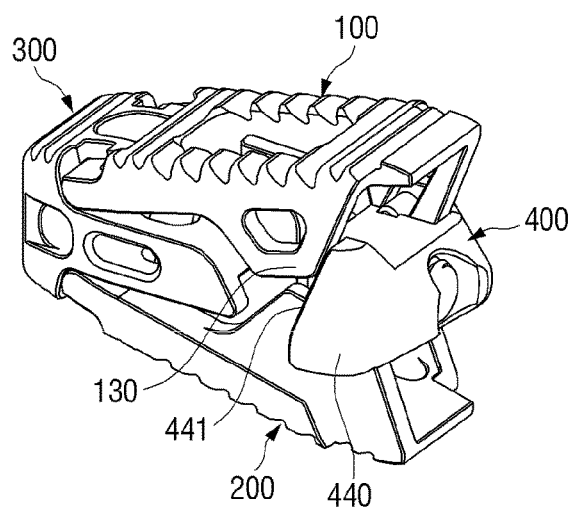
Figure 6A:
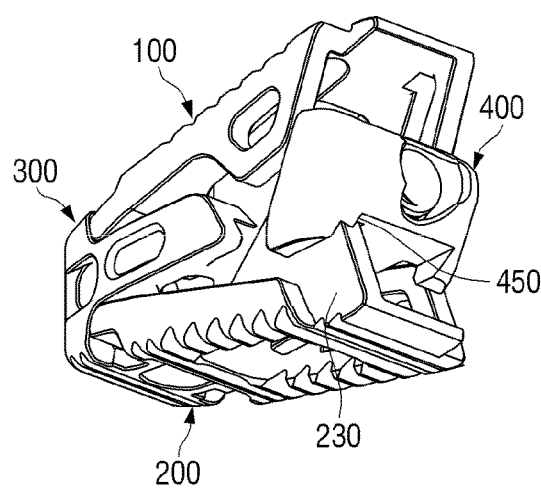
FIGS. 6A-6B are views showing a portion at which a lower plate and the block according to the embodiment of the present invention are in contact with each other.
Figure 6B:
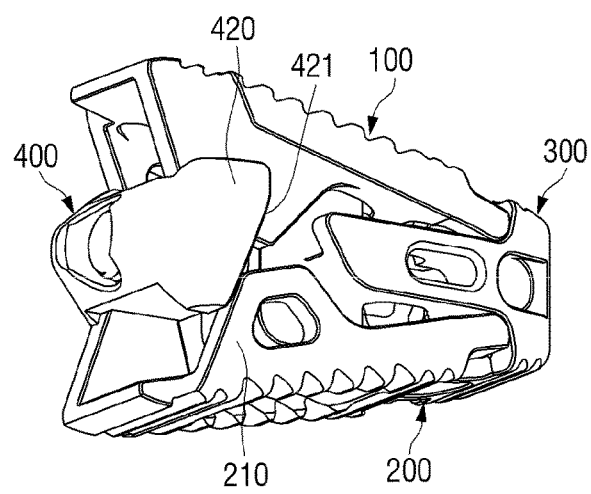

FIG. 3 is a view showing the block according to the embodiment of the present invention, seen from the front, FIG. 4 is a view showing the block according to the embodiment of the present invention, seen from the rear, FIGS. 5A-5B are views showing a portion at which the upper plate and the block according to the embodiment of the present invention are in contact with each other, and FIGS. 6A-6B are views showing a portion at which the lower plate and the block according to the embodiment of the present invention are in contact with each other.

As shown in the drawing, the block 400 includes a block body 410 having the block hole 411 formed in the center thereof, a first inclined part 420 coupled to one side of the block body 410, the first inclined part 420 having a first inclined surface 421 inclined at a predetermined inclination angle, a second inclined part 440 coupled to the other side of the block body 410, the second inclined part 440 having a second inclined surface 441 inclined at a predetermined inclination angle, a first inclined accommodation groove 430 formed between the block body 410 and the first inclined part 420, the first inclined accommodation groove 430 inclined at a predetermined inclination angle, and a second inclined accommodation groove 450 formed between the block body 410 and the second inclined part 440, the second inclined accommodation groove 450 inclined at a predetermined inclination angle.

The block body 410 is formed in a hexahedral shape overall, and the block hole 411 is formed through the center of the block body 410 in the forward-and-rearward direction. The bolt body 510 of the driving bolt 500 is accommodated in the block hole 411. A front inclined surface 412 oriented at a predetermined angle relative to the center of the block body 410 is formed on the front surface of the block body 410.

The first inclined part 420 is coupled to the left side of the block body 410 and the second inclined part 440 is coupled to the right side of the block body 410. The first inclined part 420 is formed in an inverted triangle shape so that the first inclined surface 421 is inclined downwards and forwards at a predetermined inclination angle, and the second inclined part 440 is formed in a triangular shape so that the second inclined surface 441 is inclined upwards and forwards at a predetermined inclination angle.

The first inclined accommodation groove 430 is formed between the block body 410 and the first inclined part 420, and the second inclined accommodation groove 450 is formed between the block body 410 and the second inclined part 440. The first inclined accommodation groove 430 is formed to be inclined upwards and forwards at a predetermined inclination angle, and the second inclined accommodation groove 450 is formed to be inclined downwards and forwards at a predetermined inclination angle.

That is, the first inclined surface 421 and the second inclined surface 441 are formed to have inclination angles in opposite directions to each other, and the first inclined accommodation groove 430 and the second inclined accommodation groove 450 are formed to have inclination angles in opposite directions to each other.

In this case, it is preferable that the first inclined surface 421 of the first inclined part 420 and the second inclined accommodation groove 450 be disposed parallel to each other, and that the second inclined surface 441 of the second inclined part 440 and the first inclined accommodation groove 430 be disposed parallel to each other.

The first inclined part 420 or the second inclined part 440 has a restraint hole 422 or 442 formed therein. As shown in FIGS. 1A-1B, a restraint pin 460 may be inserted into the restraint hole 422 or 442, and the restraint pin 460 may be oriented in the transverse direction between the first inclined part 420 or the second inclined part 440 and the block body 410.

A long hole 120 or 220, which is elongated in the vertical direction, is formed in a side portion of the upper plate 100 or the lower plate 200 so as to be aligned with the position of the restraint pin 460. The restraint pin 460 is slidably inserted into and accommodated in the long hole 120 or 220. Accordingly, the vertical angle that the upper plate 100 or the lower plate 200 is capable of forming may be limited. When the restraint pin 460 is located at the lowermost end of the long hole 120 in the upper plate 100, the upper plate 100 has the maximum angle; that is, the upper plate 100 is raised as far as possible.

FIG. 5A is a view showing a portion at which the upper plate and the block according to the embodiment of the present invention are in contact with each other, seen from the left side, FIG. 5B is a view showing a portion at which the upper plate and the block according to the embodiment of the present invention are in contact with each other, seen from the right side, FIG. 6A is a view showing a portion at which the lower plate and the block according to the embodiment of the present invention are in contact with each other, seen from the right side, and FIG. 6B is a view showing a portion at which the lower plate and the block according to the embodiment of the present invention are in contact with each other, seen from the left side.

As shown in FIGS. 5A-5B, the upper plate 100 has a first upper protrusion 110 coupled thereto on the left side thereof, the first upper protrusion 110 being accommodated in the first inclined accommodation groove 430. Further, the upper plate 100 has a second upper protrusion 130 coupled thereto on the right side thereof, the second upper protrusion 130 being in contact with the second inclined surface 441 of the second inclined part 440.

As described above, each of the first inclined accommodation groove 430 and the second inclined surface 441 is inclined upwards and forwards at a predetermined inclination angle. Accordingly, when the frame 300 moves forwards and the distance between the block 400 and the frame 300 is decreased, the front end of the upper plate 100 moves forwards and upwards, and the angle of the upper plate 100 with respect to the frame 300 is increased.

As shown in FIGS. 6A-6B, the lower plate 200 has a second lower protrusion 230 coupled thereto on the right side thereof, the second lower protrusion 230 being accommodated in the second inclined accommodation groove 450. Further, the lower plate 200 has a first lower protrusion 210 coupled thereto on the left side thereof, the first lower protrusion 210 being in contact with the first inclined surface 421 of the first inclined part 420.

As described above, each of the second inclined accommodation groove 450 and the first inclined surface 421 is inclined downwards and forwards at a predetermined inclination angle. Accordingly, when the frame 300 moves forwards and the distance between the block 400 and the frame 300 is decreased, the front end of the lower plate 200 moves forwards and downwards, and the angle of the lower plate 200 with respect to the frame 300 is increased.

Figure 7:
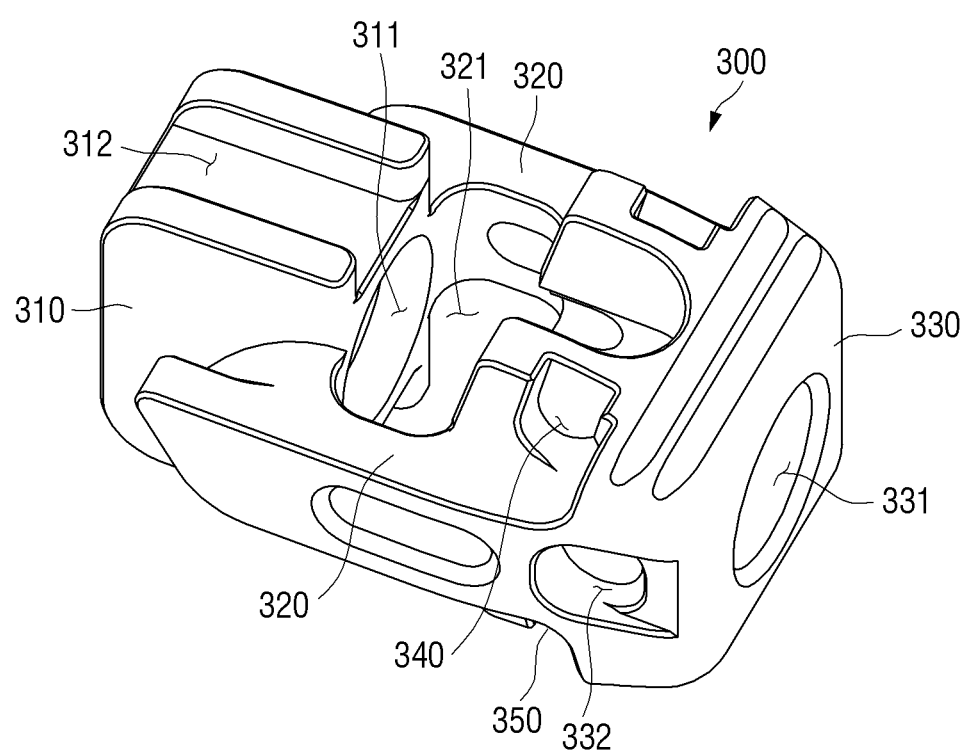
FIG. 7 is a view showing a frame according to the embodiment of the present invention.
Figure 8A:
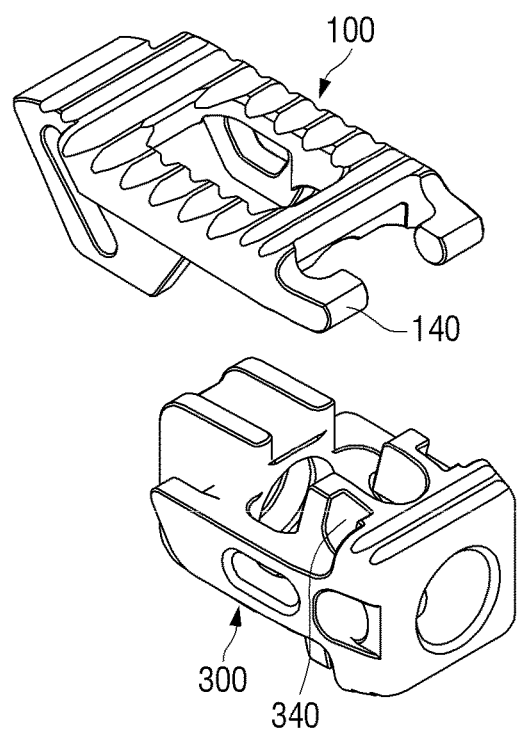
FIGS. 8A-8B are views showing the state in which the rear ends of the upper plate and the lower plate according to the embodiment of the present invention are disassembled from the frame.
Figure 8B:
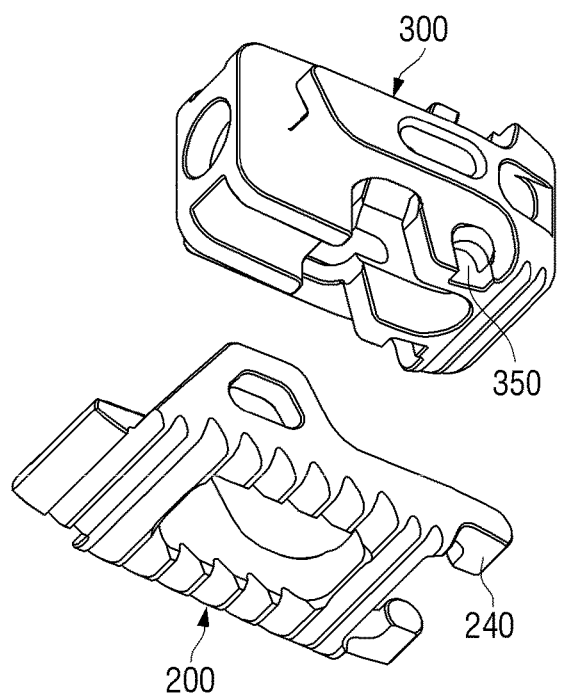
Figure 9:
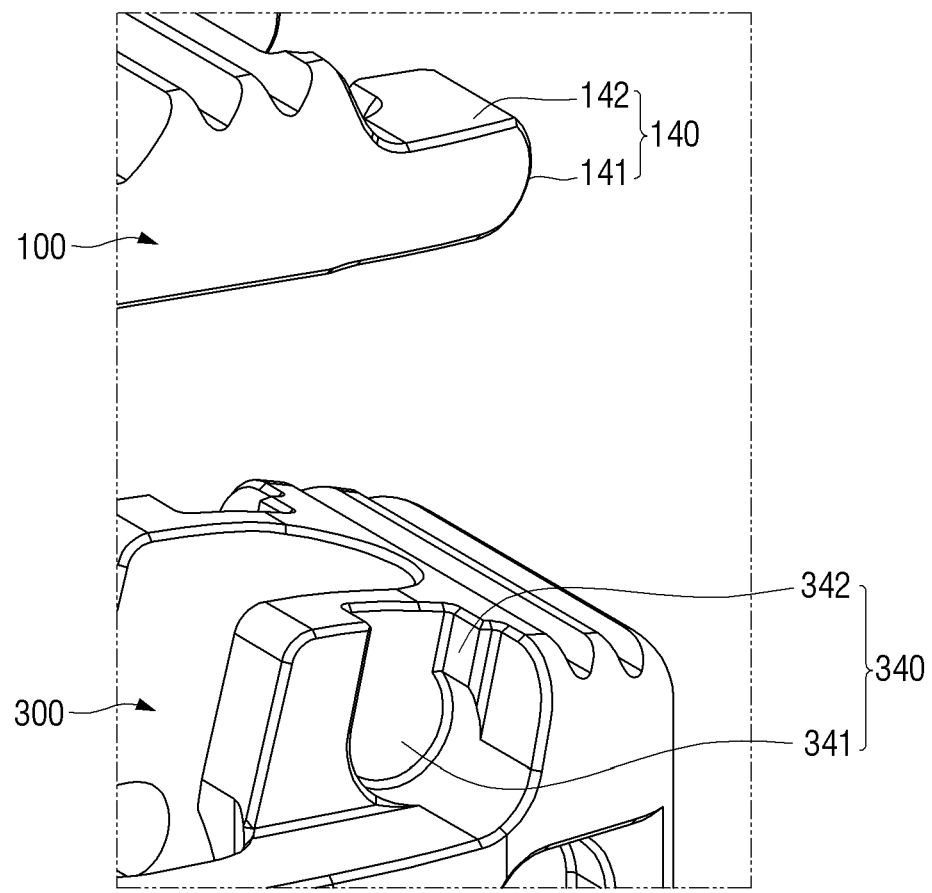
FIG. 9 is an enlarged view showing an upper hinge part of the upper plate and an upper hinge groove of the frame according to the embodiment of the present invention.
Figure 10:
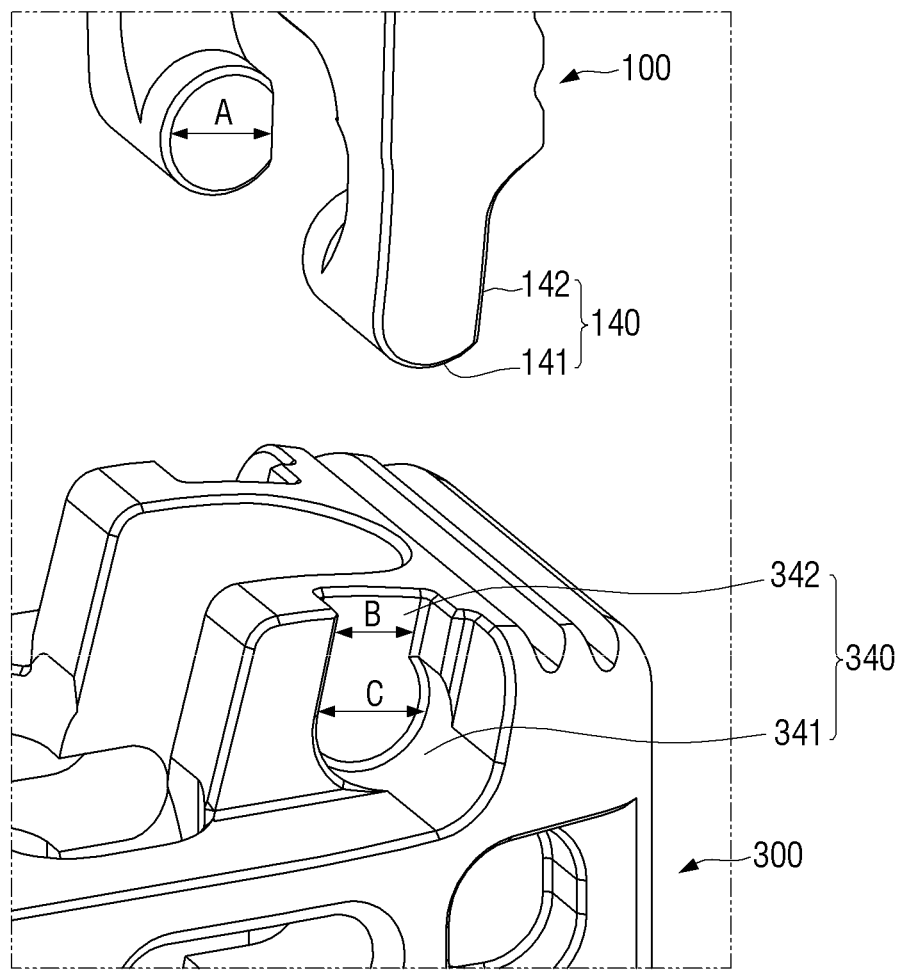
FIG. 10 is a view showing a process in which the upper hinge part according to the embodiment of the present invention is coupled into the upper hinge groove.
Figure 11:
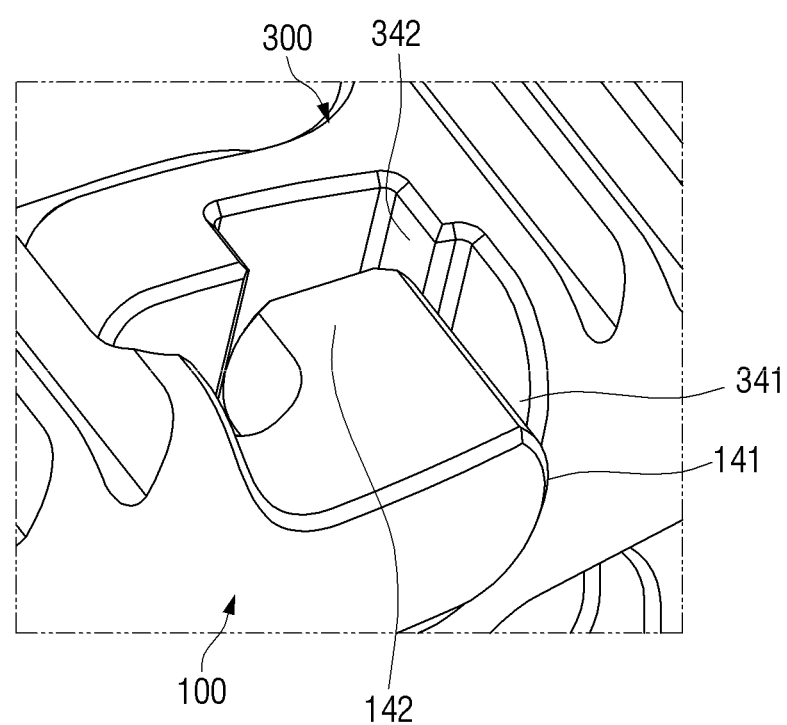
FIG. 11 is a view showing the state in which the upper hinge part according to the embodiment of the present invention is completely coupled into the upper hinge groove.

FIG. 7 is a view showing the frame according to the embodiment of the present invention, FIGS. 8A-8B are views showing the state in which the rear ends of the upper plate and the lower plate according to the embodiment of the present invention are disassembled from the frame, FIG. 9 is an enlarged view showing an upper hinge part of the upper plate and an upper hinge groove of the frame according to the embodiment of the present invention, FIG. 10 is a view showing a process in which the upper hinge part according to the embodiment of the present invention is coupled into the upper hinge groove, and FIG. 11 is a view showing the state in which the upper hinge part according to the embodiment of the present invention is completely coupled into the upper hinge groove.

FIG. 8A is a view showing the state in which the upper hinge part of the upper plate according to the embodiment of the present invention is disassembled from the upper hinge groove of the frame, and FIG. 8B is a view showing the state in which a lower hinge part of the lower plate according to the embodiment of the present invention is disassembled from a lower hinge groove of the frame.

As shown in the drawings, the frame 300 includes the front part 310, the connection part 320, and the rear part 330.

The front hole 311 is formed in the center of the front part 310 in the longitudinal direction (the forward-and-rearward direction), and bolt head 520 of the driving bolt 500 is rotatably inserted into the front hole 311.

A fusion passage 312 is formed in the upper surface of the front part 310, the lower surface thereof, or both the upper and lower surfaces thereof. The fusion passage 312 provides a passage to allow autogenous bone, allograft bone, or synthetic bone to pass therethrough.

The connection part 320 extends rearwards from the rear end of the front part 310. In the embodiment, a pair of connection parts 320 is provided, but the number thereof is not limited thereto. The internal space 321 is defined between the pair of connection parts 320.

The rear part 330 is coupled to the rear end of the connection part 320. A frame penetration hole 331 is formed in the center of the rear part 330 in the longitudinal direction (the forward-and-rearward direction), and the frame penetration hole 331 is connected to the internal space 32.

A mechanism-coupling groove 332 is formed to be recessed into a side portion of the rear part 330. The mechanism-coupling groove 332 allows the frame 300 to be coupled to a predetermined mechanism. In the embodiment, each of the mechanism-coupling grooves 332 is formed in a corresponding one of opposite sides of the rear part 330, but the present invention is not limited thereto.

As shown in FIGS. 8A-8B, at least one upper hinge groove 340 and at least one lower hinge groove 350 are formed to be recessed into the side portion of the rear part 330. The upper plate 100 has an upper hinge part 140 at the rear end thereof. Here, the upper hinge part 140 is formed to protrude so as to be inserted into and accommodated in the upper hinge groove 340. Further, the lower plate 200 has a lower hinge part 240 at the rear end thereof. Here, the lower hinge part 240 is formed to protrude so as to be inserted into and accommodated in the lower hinge groove 350. The upper plate 100 and the lower plate 200 are rotatable with respect to the upper hinge part 140 and the lower hinge part 240, respectively.

Specifically, as shown in FIG. 9, the upper hinge groove 340 includes an upper curved surface part 341 having a curved inner surface, and an upper coupling passage part 342 connected to the upper portion of the upper curved surface part 341.

In the embodiment, only the upper hinge groove 340 is shown for convenience of description, but the lower hinge groove 350 may also include a lower curved surface part (not shown) and a lower coupling passage part (not shown) in a similar manner.

Meanwhile, the upper hinge part 140 has an upper hinge curved surface 141 formed at the rear end thereof, the upper hinge curved surface 141 having a curved surface to correspond to the upper curved surface part 341 of the upper hinge groove 340. In the embodiment, only the upper hinge curved surface 141 is shown for convenience of description, but a lower hinge curved surface (not shown) may also be formed in the lower hinge part 240 in a similar manner.

The upper hinge curved surface 141 may be in contact with the upper curved surface part 341 of the upper hinge groove 340 (refer to FIG. 11). Accordingly, the upper plate 100 may rotate with respect to the frame 300 along the trajectory of the upper curved surface part 341.

The upper hinge part 140 has an upper entrance part 142 formed on the upper surface of the rear end thereof so as to enter the upper coupling passage part 342. The upper entrance part 142 has a flat surface. Accordingly, the rear end of the upper hinge part 140 including the upper hinge curved surface 141 and the upper entrance part 142 has a circular cross-section, one side of which is partially cut off. In the embodiment, only the upper entrance part 142 is shown for convenience of description, but a lower entrance part (not shown) may also be formed in the lower hinge part 240 in a similar manner.

As shown in FIG. 10, the width A of the upper entrance part 142 is formed to be equal to or smaller than the width B of the upper coupling passage part 342, and the width B of the upper coupling passage part 342 is formed to be smaller than the maximum width C of the upper curved surface part 341.

Since the width B of the upper coupling passage part 342 is formed to be smaller than the maximum width C of the upper curved surface part 341, the upper hinge part 140 may enter the upper coupling passage part 342 only in the direction of the upper entrance part 142, and may not enter the same in another direction.

That is, the upper hinge part 140 may enter the inside of the upper coupling passage part 342 only when the upper plate 100 is disposed at an angle of approximately 90 degrees with respect to the frame 300, in which state the upper entrance part 142 is in contact with the upper coupling passage part 342.

As shown in FIG. 11, after the upper entrance part 142 passes through the upper coupling passage part 342 and is disposed inside the upper curved surface part 341, the upper plate 100 is disposed substantially parallel to the frame 300, and the upper hinge curved surface 141 is in contact with the upper curved surface part 341.

In this case, as described above, the maximum width C of the upper curved surface part 341 is formed to be larger than the width B of the upper coupling passage part 342. Accordingly, unless the upper plate 100 is disposed at the angle of approximately 90 degrees with respect to the frame 300, the upper hinge part 140 may not pass through the upper coupling passage part 342 and may not be separated therefrom. That is, the upper hinge part 140 remains held in the upper curved surface part 341.

Figure 12:
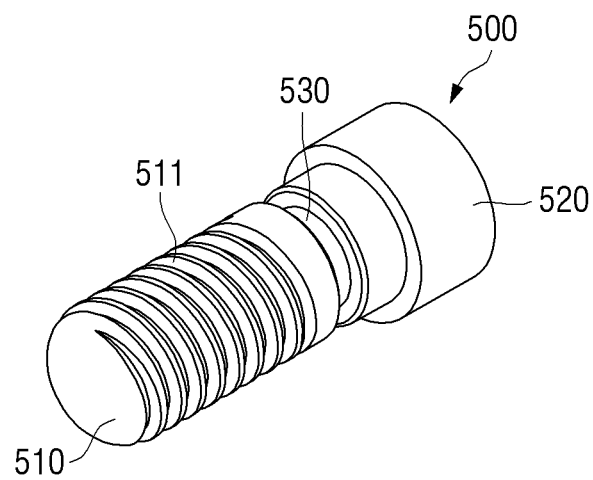
FIG. 12 is a view showing a driving bolt according to the embodiment of the present invention.
Figure 13:
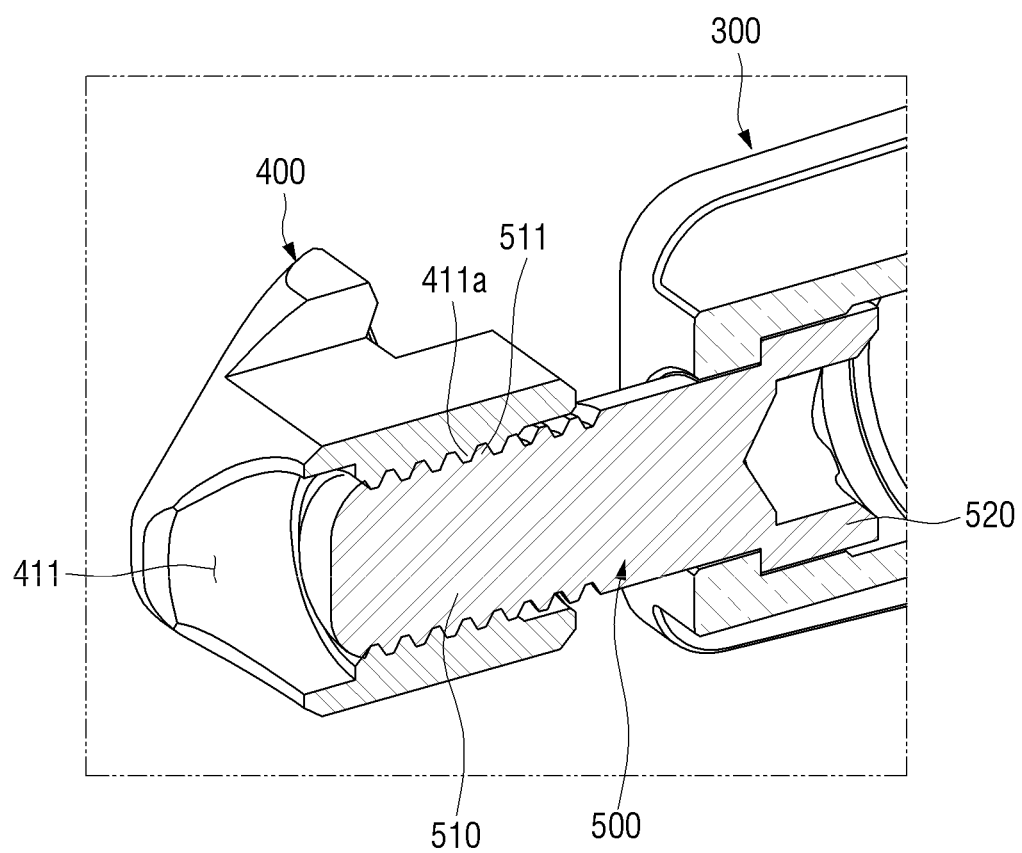
FIG. 13 is a partial cross-sectional view showing the state in which the driving bolt according to the embodiment of the present invention is inserted into the block.
Figure 14:
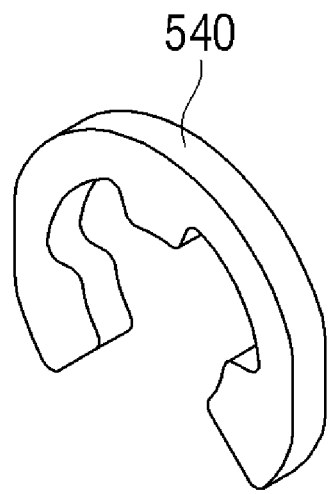
FIG. 14 is a view showing a fixing ring according to the embodiment of the present invention.
Figure 15:
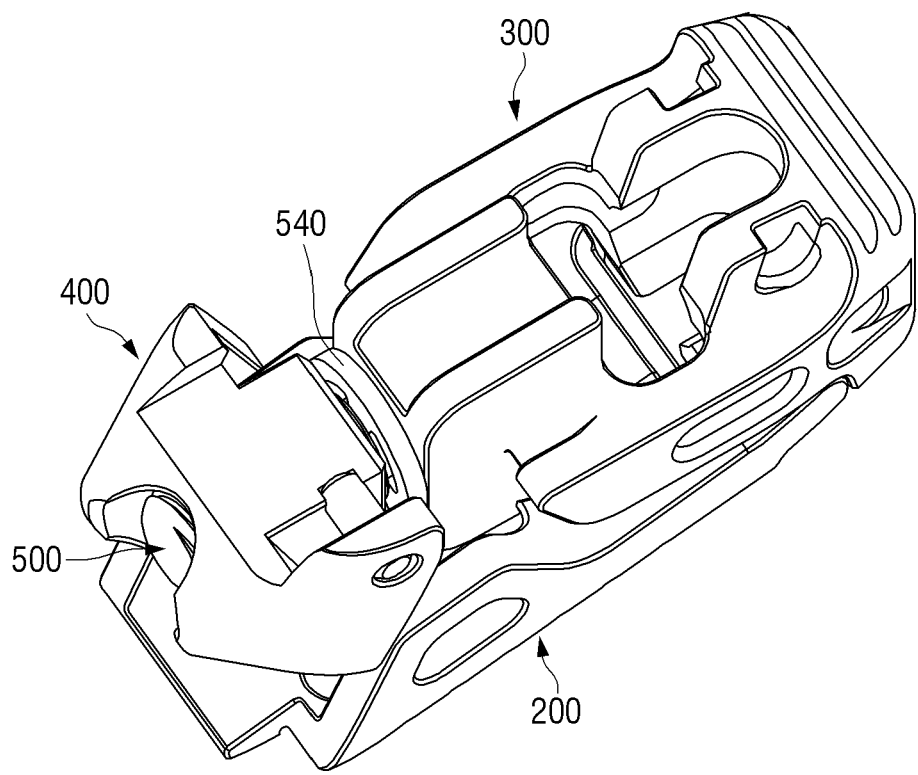
FIG. 15 is a view showing the state in which the fixing ring is coupled to the driving bolt according to the embodiment of the present invention.
Figure 16:
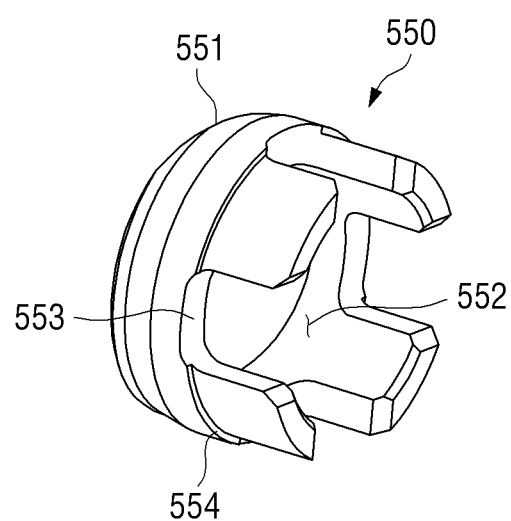
FIG. 16 is a view showing a fixing cap according to the embodiment of the present invention.
Figure 17A:
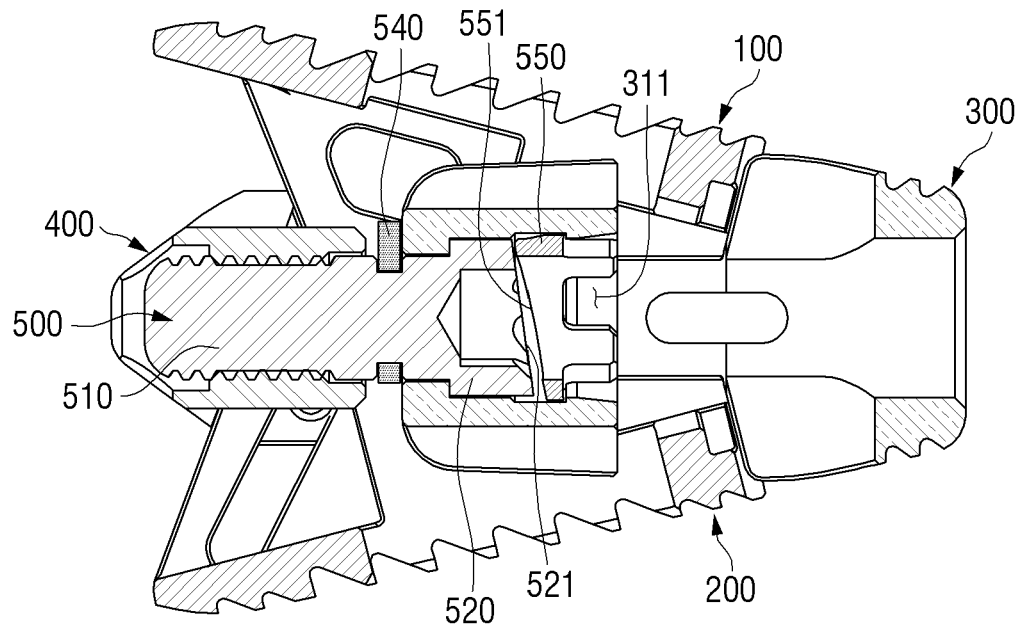
FIGS. 17A-17B are partial cross-sectional views showing the state in which the fixing cap according to the embodiment of the present invention is inserted into the frame.
Figure 17B:
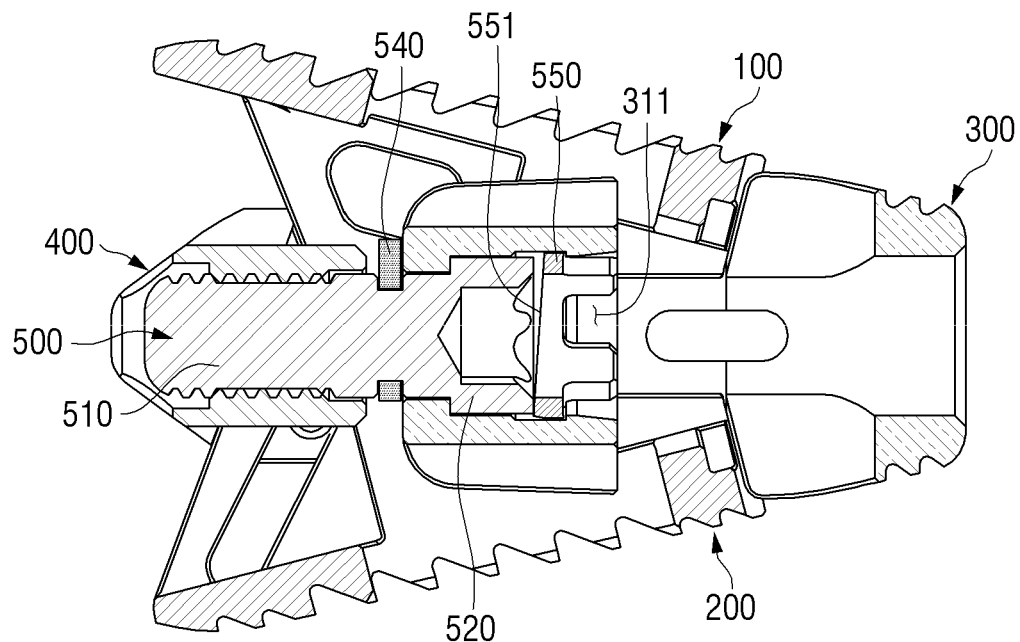
Figure 18:
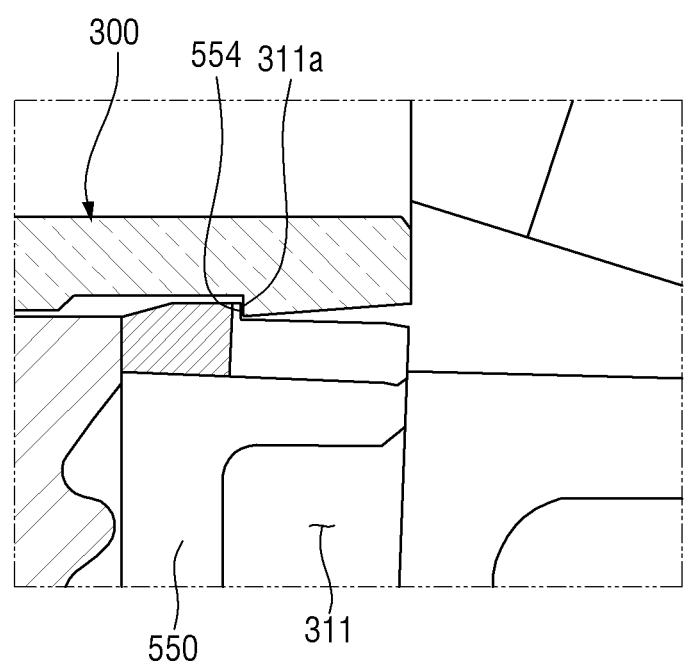
FIG. 18 is a partial cross-sectional view showing the state in which the fixing end of the fixing cap according to the embodiment of the present invention is in contact with and supported by the front end.
Figure 19:
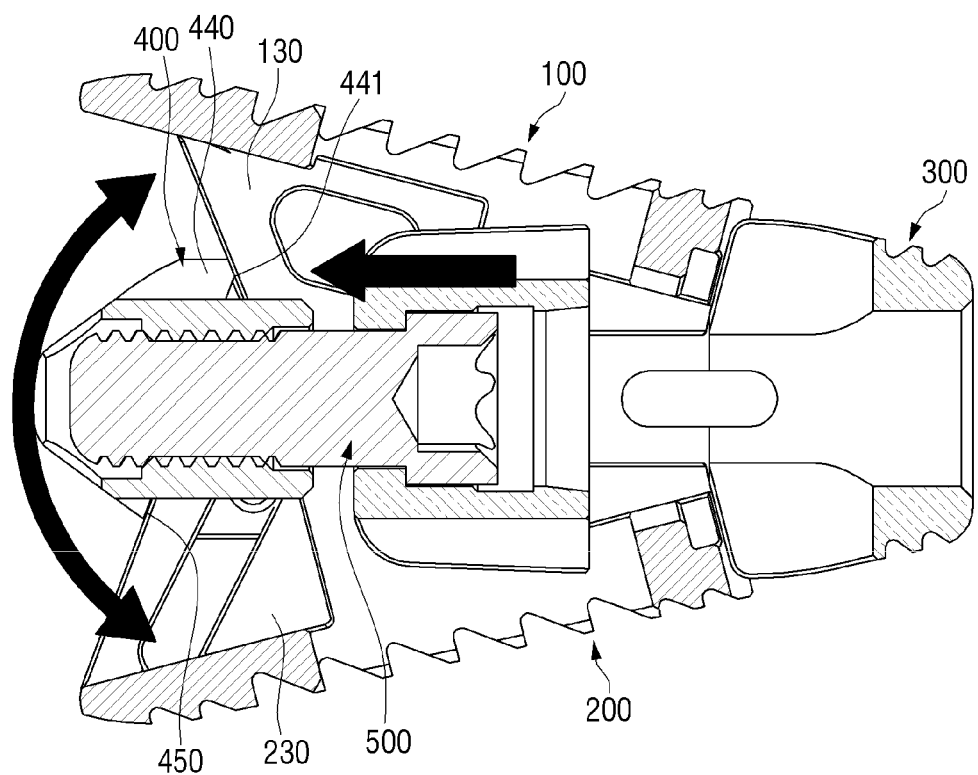
FIG. 19 is a cross-sectional view showing the state in which the angle of each of the upper plate and the lower plate according to the embodiment of the present invention with respect to the frame is increased.
Figure 20:
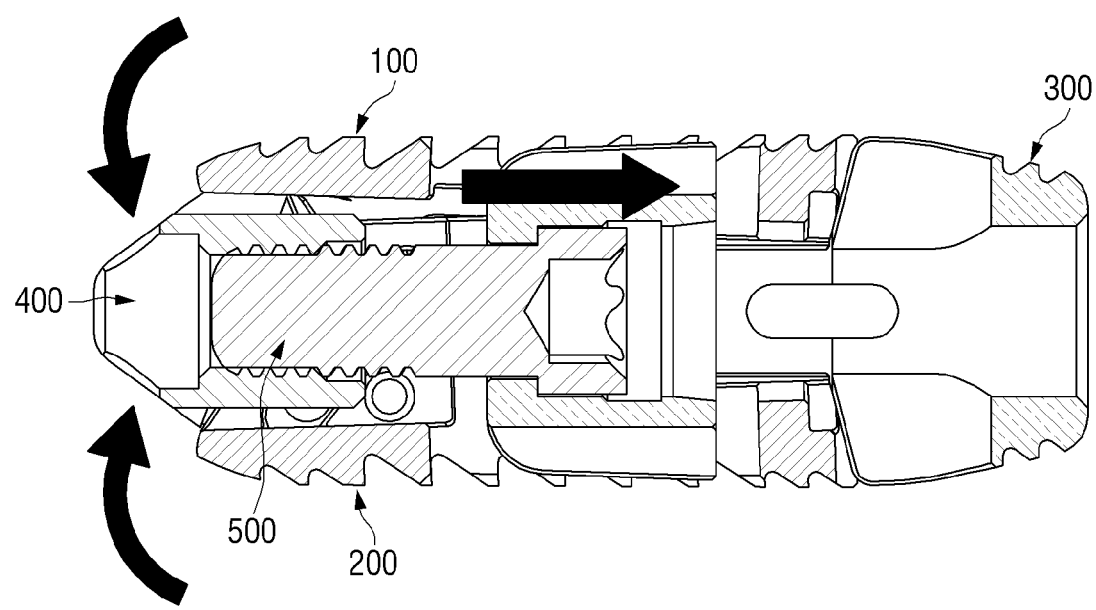
FIG. 20 is a cross-sectional view showing the state in which the angle of each of the upper plate and the lower plate according to the embodiment of the present invention with respect to the frame is decreased.
Figure 20:
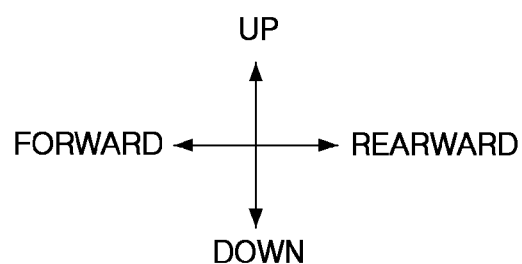

FIG. 12 is a view showing a driving bolt according to the embodiment of the present invention, FIG. 13 is a partial cross-sectional view showing the state in which the driving bolt according to the embodiment of the present invention is inserted into the block, FIG. 14 is a view showing a fixing ring according to the embodiment of the present invention, FIG. 15 is a view showing the state in which the fixing ring is coupled to the driving bolt according to the embodiment of the present invention, FIG. 16 is a view showing a fixing cap according to the embodiment of the present invention, FIGS. 17A-17B are partial cross-sectional views showing the state in which the fixing cap according to the embodiment of the present invention is inserted into the frame, FIG. 18 is a partial cross-sectional view showing the state in which the fixing end of the fixing cap according to the embodiment of the present invention is in contact with and supported by the front end, FIG. 19 is a cross-sectional view showing the state in which the angle of each of the upper plate and the lower plate according to the embodiment of the present invention with respect to the frame is increased, and FIG. 20 is a cross-sectional view showing the state in which the angle of each of the upper plate and the lower plate according to the embodiment of the present invention with respect to the frame is decreased.

As shown in the drawings, the driving bolt 500 includes the bolt body 510, the bolt head 520, and a fixing groove 530. The bolt body 510 is formed in a cylindrical shape, and has the male threads 511 formed on the outer circumferential surface thereof. The bolt head 520 is coupled to the rear end of the bolt body 510, and has a diameter larger than that of the bolt body 510. The fixing groove 530 is formed between the bolt body 510 and the bolt head 520, and has a diameter smaller than that of the bolt body 510.

As shown in FIG. 13, the block 400 has the block hole 411 formed in the center thereof in the longitudinal direction (the forward-and-rearward direction), and the block hole 411 has female threads 411*a* formed on the inner surface thereof so as to be engaged with the male threads 511 of the driving bolt 500.

When the driving bolt 500 is rotated, the male threads 511 of the driving bolt 500 are engaged with the female threads 411*a* of the block hole 411. Accordingly, the driving bolt 500 and the frame 300 connected thereto may move forwards or rearwards in the direction of the block 400.

As shown in FIGS. 14 and 15, a fixing ring 540 is coupled to the fixing groove 530. The fixing ring 540 is formed in a 'C' shape with one side thereof open, and may be inserted into and accommodated in the fixing groove 530, or may be separated from the fixing groove 530.

When the fixing ring 540 is coupled to the fixing groove 530, the rear surface of the fixing ring 540 is in contact with the front surface of the frame 300. The bolt head 520, having a diameter larger than that of the bolt body 510, is accommodated in the frame 300, and the fixing ring 540 is in contact with the front surface of the frame 300. Accordingly, the driving bolt 500 is rotatably coupled to the frame 300 to pull the frame 300.

As shown in FIGS. 16 and 17, a fixing cap 550 to come into contact with the rear end of the bolt head 520 may be further accommodated in the front hole 311 in the front part 310 in the frame 300 so as to be rotatable therein.

FIG. 17A is a partial cross-sectional view showing the state in which the fixing cap according to the embodiment of the present invention is in contact with the rear end of the bolt head, and FIG. 17B is a partial cross-sectional view showing the state in which the fixing cap according to the embodiment of the present invention rotates to come into close contact with the rear end of the bolt head.

A bolt inclined surface 521 inclined at a predetermined inclination angle is formed at the rear end of the bolt head 520. A fixing inclined surface 551 is formed at the front end of the fixing cap 550 to come into contact with the rear end of the bolt head 520, the fixing inclined surface 551 being formed so as to correspond to the shape of the bolt inclined surface 521.

When the angle of each of the upper plate 100 and the lower plate 200 with respect to the frame 300 is set by operating the driving bolt 500 as shown in FIG. 17A, the fixing inclined surface 551 presses the bolt inclined surface 521 by rotating the fixing cap 550 inserted into the front hole 311, and the fixing inclined surface 551 and the bolt inclined surface 521 are kept in close contact with each other, as shown in FIG. 17B. Accordingly, the driving bolt 500 is firmly fixed without loosening.

In this case, the fixing cap 550 includes a fixing hole 552 opening in the longitudinal direction (the forward-and-rearward direction) of the frame 300, and a plurality of fixing rotation grooves 553 are recessed into a side portion of the fixing cap 550 so as to hold and rotate the fixing cap 550. In the embodiment, the number of fixing rotation grooves 553 is four, but the number thereof is not limited thereto.

A fixing end 554 is formed to protrude in the shape of a ring from the side portion of the fixing cap 550. As shown in FIG. 18, the fixing end 554 is in contact with and supported by a front end 311*a* formed to protrude from the inside of the front hole 311. Accordingly, the fixing cap 550 is prevented from becoming separated from the front hole 311.

The operation process of the angle-expandable spinal cage according to the present invention will be described. As shown in FIG. 19, when the driving bolt 500 is moved forwards by rotating the driving bolt 500, the frame 300 coupled to the driving bolt 500 also moves forwards. When the frame 300 moves forwards, the upper plate 100 and the lower plate 200 also move forwards.

When the upper plate 100 and the lower plate 200 move forwards, the first upper protrusion 110 and the second upper protrusion 130 of the upper plate 100 move forwards and upwards in the state of remaining in contact with the first inclined accommodation groove 430 and the second inclined surface 441, respectively, and the first lower protrusion 210 and the second lower protrusion 230 of the lower plate 200 move forwards and downwards in the state of remaining in contact with the first inclined surface 421 and the second inclined accommodation groove 450, respectively. Accordingly, the angle of each of the upper plate 100 and the lower plate 200 with respect to the frame 300 is increased.

On the other hand, as shown in FIG. 20, when the driving bolt 500 is moved rearwards by rotating the driving bolt 500, the frame 300 coupled to the driving bolt 500 also moves rearwards. When the frame 300 moves rearwards, the upper plate 100 and the lower plate 200 also move rearwards.

When the upper plate 100 and the lower plate 200 move rearwards, the first upper protrusion 110 and the second upper protrusion 130 of the upper plate 100 move rearwards and downwards in the state of remaining in contact with the first inclined accommodation groove 430 and the second inclined surface 441, respectively, and the first lower protrusion 210 and the second lower protrusion 230 of the lower plate 200 move rearwards and upwards in the state of remaining in contact with the first inclined surface 421 and the second inclined accommodation groove 450, respectively. Accordingly, the angle of each of the upper plate 100 and the lower plate 200 with respect to the frame 300 is decreased.

As is apparent from the above description, an angle-expandable spinal cage of the present invention having the above-described configuration has an effect of making it possible to increase or decrease the angle of each of an upper plate and a lower plate with respect to a frame by adjusting the distance between a block and the frame.

In other words, according to the present invention, the angle-expandable spinal cage may be implanted into an affected area of a patient suffering from a spinal injury in the state in which the angle of each of the upper plate and the lower plate with respect to the frame is reduced to the minimum angle, and the angle of the angle-expandable spinal cage may be expanded in the affected area, thereby having an effect of being usefully used for minimally invasive surgery.

Although preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An angle-expandable spinal cage comprising:
   an upper plate and a lower plate disposed to face each other;
   a frame disposed between the upper plate and the lower plate, the frame having a space formed therein;
   a block disposed between the upper plate and the lower plate and disposed in front of the frame; and
   a driving bolt having one end thereof connected to the frame and a remaining end thereof connected to the block,
   wherein an angle of each of the upper plate and the lower plate with respect to the frame is increased or decreased when a distance between the block and the frame is adjusted by operating the driving bolt,
   wherein the driving bolt comprises:
   a bolt body having male threads formed on an outer circumferential surface thereof; and
   a bolt head formed at an end of the bolt body, the bolt head having a diameter larger than a diameter of the bolt body,
   wherein the bolt head is accommodated in a front hole formed to penetrate through the frame, and
   wherein the front hole further accommodates a fixing cap to come into contact with an end of the bolt head, the fixing cap being rotatable in the front hole.

2. The angle-expandable spinal cage according to claim 1, wherein the block comprises:
   a block body having a block hole formed in a center thereof;
   a first inclined part coupled to one side of the block body, the first inclined part having a first inclined surface inclined at a predetermined inclination angle;
   a second inclined part coupled to the other side of the block body, the second inclined part having a second inclined surface inclined at a predetermined inclination angle;
   a first inclined accommodation groove formed between the block body and the first inclined part, the first inclined accommodation groove being inclined at a predetermined inclination angle; and
   a second inclined accommodation groove formed between the block body and the second inclined part, the second inclined accommodation groove being inclined at a predetermined inclination angle.

3. The angle-expandable spinal cage according to claim 2, wherein:
   the upper plate has a first upper protrusion coupled to one side thereof, the first upper protrusion being accommodated in the first inclined accommodation groove, and a second upper protrusion coupled to the other side thereof, the second upper protrusion being in contact with the second inclined surface of the second inclined part, and
   the lower plate has a first lower protrusion coupled to one side thereof, the first lower protrusion being in contact with the first inclined surface of the first inclined part, and a second lower protrusion coupled to the other side thereof, the second lower protrusion being accommodated in the second inclined accommodation groove.

4. The angle-expandable spinal cage according to claim 2, wherein the first inclined surface of the first inclined part and the second inclined accommodation groove are disposed parallel to each other, and the second inclined surface of the second inclined part and the first inclined accommodation groove are disposed parallel to each other.

5. The angle-expandable spinal cage according to claim 2, wherein:
   the first inclined part or the second inclined part and the block body have a restraint pin disposed therebetween and coupled thereto in a transverse direction, and
   the upper plate or the lower plate has a long hole formed in a side portion thereof, the long hole being formed to be vertically elongated to correspond to a position of the restraint pin,
   wherein the restraint pin is inserted into and accommodated in the long hole so as to be slidable therein.

6. The angle-expandable spinal cage according to claim 1, wherein the frame comprises:
   a front part having the front hole formed therein, the front hole allowing one end of the driving bolt to be inserted thereinto;
   a connection part extending in a longitudinal direction from one end of the front part; and
   a rear part coupled to one end of the connection part.

7. The angle-expandable spinal cage according to claim 6, wherein:
   the rear part has at least one upper hinge groove and at least one lower hinge groove formed to be recessed into a side portion thereof, and
   the upper plate has an upper hinge part at one end thereof, the upper hinge part being formed to protrude so as to be inserted into and accommodated in the upper hinge groove, and the lower plate has a lower hinge part at one end thereof, the lower hinge part being formed to protrude so as to be inserted into and accommodated in the lower hinge groove,
   wherein the upper plate and the lower plate are rotatable with respect to the upper hinge part and the lower hinge part, respectively.

8. The angle-expandable spinal cage according to claim 7, wherein:
   the upper hinge groove comprises an upper curved surface part having a curved inner surface, and an upper coupling passage part connected to an upper portion of the upper curved surface part, and
   the lower hinge groove comprises a lower curved surface part having a curved inner surface, and a lower coupling passage part connected to a lower portion of the lower curved surface part.

9. The angle-expandable spinal cage according to claim 8, wherein:
   the upper hinge part has an upper hinge curved surface formed at one end thereof, the upper hinge curved surface having a curved surface to correspond to the upper curved surface part of the upper hinge groove, and
   the lower hinge part has a lower hinge curved surface formed at one end thereof, the lower hinge curved surface having a curved surface to correspond to the lower curved surface part of the lower hinge groove.

10. The angle-expandable spinal cage according to claim 9, wherein the upper hinge part has an upper entrance part formed at one end thereof so as to enter the upper coupling passage part, and the lower hinge part has a lower entrance part formed at one end thereof so as to enter the lower coupling passage part.

11. The angle-expandable spinal cage according to claim 10, wherein:
   the upper entrance part has a width formed to be equal to or smaller than a width of the upper coupling passage part, and the upper coupling passage part has the width formed to be smaller than a maximum width of the upper curved surface part, and the lower entrance part has a width formed to be equal to or smaller than a width of the lower coupling passage part, and the lower coupling passage part has the width formed to be smaller than a maximum width of the lower curved surface part.

12. The angle-expandable spinal cage according to claim 6, wherein the front part has a fusion passage formed in an upper surface thereof or a lower surface thereof.

13. The angle-expandable spinal cage according to claim 6, wherein the rear part has a frame penetration hole formed therein in the longitudinal direction, wherein the frame penetration hole is connected to an internal space defined by the connection part.

14. The angle-expandable spinal cage according to claim 6, wherein the rear part has a mechanism-coupling groove formed in a side portion thereof, the mechanism-coupling groove being formed to be recessed.

15. The angle-expandable spinal cage according to claim 1, further comprising:

a fixing groove formed between the bolt body and the bolt head, the fixing groove having a diameter smaller than the diameter of the bolt body; and a fixing ring inserted into and accommodated in the fixing groove, the fixing ring being formed in a 'C' shape with one side thereof open.

16. The angle-expandable spinal cage according to claim 1, wherein:

the bolt head has a bolt inclined surface formed at an end thereof, the bolt inclined surface being inclined at a predetermined inclination angle, and the fixing cap, contacting the end of the bolt head, has a fixing inclined surface formed at an end thereof, the fixing inclined surface being formed to correspond to a shape of the bolt inclined surface, wherein the bolt inclined surface and the fixing inclined surface are kept in close contact with each other when the fixing cap rotates.

17. The angle-expandable spinal cage according to claim 1, wherein the front hole has a front end formed therein to allow a fixing end formed to protrude from a side portion of the fixing cap to be in contact with and supported by the front end, the front end being formed to protrude from an inside of the front hole.

18. The angle-expandable spinal cage according to claim 1, wherein the fixing cap has a plurality of fixing rotation grooves formed in a side portion thereof so that the fixing cap is rotatable, the plurality of fixing rotation grooves being formed to be recessed into the side portion.

* * * * *